US011774246B2

(12) United States Patent
Santos et al.

(10) Patent No.: US 11,774,246 B2
(45) Date of Patent: Oct. 3, 2023

(54) CORRECTION OF HEADING ERRORS OF INERTIAL MEASUREMENT UNITS OF A MOTION TRACKING SYSTEM

(71) Applicant: SWORD HEALTH, S.A., Oporto (PT)

(72) Inventors: Pedro Henrique Oliveira Santos, Oporto (PT); Luís Ungaro Pinto Coelho, Oporto (PT); Marta Maria Ramalho Ferreira, Oporto (PT); Ana Clara Ferreira Matos, Oporto (PT); Pablo Peñas, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 17/941,764

(22) Filed: Sep. 9, 2022

(65) Prior Publication Data

US 2023/0003528 A1    Jan. 5, 2023

Related U.S. Application Data

(63) Continuation of application No. PCT/EP2021/056233, filed on Mar. 11, 2021.

(30) Foreign Application Priority Data

Mar. 11, 2020  (EP) ..................... 20398002

(51) Int. Cl.
*A61B 5/11* (2006.01)
*G01C 21/16* (2006.01)
(Continued)

(52) U.S. Cl.
CPC ............ *G01C 21/16* (2013.01); *A61B 5/1126* (2013.01); *A61B 5/6828* (2013.01);
(Continued)

(58) Field of Classification Search
CPC ...... G01C 21/16; G01C 25/005; A61B 5/1126; A61B 5/6828; A61B 2505/09;
(Continued)

(56) References Cited

U.S. PATENT DOCUMENTS

2019/0117128 A1    4/2019  Chen et al.

FOREIGN PATENT DOCUMENTS

WO   WO-2019243438 A1    12/2019
WO   WO-2021180869 A1    9/2021

OTHER PUBLICATIONS

EP Application No. 20398002.4 Extended European Search Report dated Sep. 11, 2020.
(Continued)

*Primary Examiner* — Robert R Raevis
(74) *Attorney, Agent, or Firm* — Wilson Sonsini Goodrich & Rosati

(57) ABSTRACT

A method comprising: digitally processing orientation measurements provided by each of first and second inertial measurement units, the first and second units being arranged on first and second body members of a person, respectively, according to a predetermined unit arrangement, and the first and second body members being connected by a joint; the measurements are digitally processed such that the computing device at least: computes a length vector of a segment of the first body member based on a first orientation measurement of the first unit; defines a joint axis plane of the joint based on a second orientation measurement of the second unit; and computes a heading rotation value for making the first orientation measurement to be contained within the joint axis plane defined; and the method further comprising digitally modifying the first orientation measurement or the second orientation measurement by applying a rotation at
(Continued)

least based on the heading rotation value computed. Also, a motion tracking system and a computer program product.

20 Claims, 6 Drawing Sheets

(51) Int. Cl.
*A61B 5/00* (2006.01)
*G01C 25/00* (2006.01)
*G01P 13/00* (2006.01)

(52) U.S. Cl.
CPC ............ *G01C 25/005* (2013.01); *G01P 13/00* (2013.01); *A61B 2505/09* (2013.01); *A61B 2560/0223* (2013.01); *A61B 2562/0219* (2013.01); *A61B 2562/0223* (2013.01)

(58) Field of Classification Search
CPC .... A61B 2560/0223; A61B 2562/0219; A61B 2562/0223; A61B 5/112; A61B 5/1123; A61B 5/6829; A61B 5/6824; G01P 13/00
USPC ..... 73/1.38, 1.77, 865.4; 702/19, 33, 92, 93, 702/96, 104, 141, 150, 151; 600/595
See application file for complete search history.

(56) References Cited

OTHER PUBLICATIONS

PCT/EP2021/056233 International Search Report and Written Opinion dated Aug. 5, 2021.

CORRECTION OF HEADING ERRORS OF INERTIAL MEASUREMENT UNITS OF A MOTION TRACKING SYSTEM

CROSS-REFERENCE TO RELATED APPLICATIONS

This application is a continuation of International Application No. PCT/EP2021/056233, filed internationally on Mar. 11, 2021, which claims priority to European Application No. 20398002.4, filed on Mar. 11, 2020, all of which are hereby incorporated by reference in their entireties.

TECHNICAL FIELD

The present invention relates to the field of systems for tracking motion of a person. More particularly, the invention relates to correction of heading errors present in measurements of inertial measurement units worn by a tracked person.

STATE OF THE ART

Motion tracking or motion capture is becoming a key technique in different applications in which the movement of a target such as a person is an important part in one or more processes of the applications.

An application growing in popularity is the physical rehabilitation of people while being monitored with a motion tracking system. The motion tracking system enables the physical rehabilitation of a person without the presence of a therapist. The person may improve the physical condition thereof by performing a number of physical exercises even if not directly supervised by the therapist but by the motion tracking system, hence the person may even perform the exercises at home, for example. The motion tracking system may include IMUs, i.e. inertial measurement units, for motion tracking of a target; the IMUs are adapted to be arranged on the target and include one or more sensing devices such as gyroscopes, accelerometers, magnetometers, etc. A computing device connected to the IMUs processes the measurements of one or several of these sensing devices for determining the movement sequence of the target, at least the movement sequence of the tracked parts of the target (i.e. those with an IMU arranged thereon).

In order to determine the movement sequence, the computing device provides heading estimates for the different IMUs (based on the measurements thereof) for establishing the orientation of the tracked body members. These heading estimates, however, are prone to heading errors due to cumulative errors in the sensing devices or magnetic disturbances that both influence the orientation measurements provided by the IMUs. Likewise, the arrangement of IMUs on the body members results, in some cases, in soft tissue artifacts and/or IMU misplacement. Soft tissue artifacts are relative displacements or changes in orientation of the IMUs due to the behavior of the soft tissues of the body member where the IMU is arranged on, thereby causing changes in the local axis of the IMU that describes the axis of the body member or a joint connected to the body member. For IMU misplacement it is meant the incorrect placement of the IMU on the body member with respect to a placement of the IMU as expected by the computing device for proper tracking of the movement and/or orientation of the concerned body member, thus if the computing expects an IMU to be arranged e.g. on the center of a body member with respect to a horizontal axis but the person arranges it displaced from the center of said body member, the orientation measurements provided by the IMU will result in orientation estimates that are not accurate. Both soft tissue artifacts and IMU misplacement cause the provision of an incorrect movement sequence unless the heading errors are corrected and the deviations compensated for.

There is an interest in having motion tracking systems capable of determining the existence of any such deviation in a heading estimate or heading error for correction of the same arising from orientation measurements of an IMU that may be affected by heading errors. By reducing the deviation and/or heading error, the movement sequence provided may be more accurate, thereby reducing the probability of incorrect assessment of the physical rehabilitation exercises performed by the person, something that, in turn, reduces the risk of injury. Further, there is also an interest in correcting the deviation and/or heading error without carrying out a calibration procedure, whenever possible, so that the motion tracking system is easier to use and operation thereof is not or is less cumbersome.

DESCRIPTION OF THE INVENTION

A first aspect of the invention relates to a method comprising:

digitally processing, by a computing device of a motion tracking system, orientation measurements provided by each of first and second inertial measurement units of the motion tracking system, each of the first and second units at least comprises an accelerometer and a gyroscope, the first and second units being arranged on first and second body members of a person, respectively, according to a predetermined unit arrangement, and the first and second body members being connected by a joint;

the measurements are digitally processed such that the computing device at least:

computes a length vector of a segment of the first body member based on a first orientation measurement of the first unit;

defines a joint axis plane of the joint based on a second orientation measurement of the second unit; and computes a heading rotation value for making the first orientation measurement to be contained within the joint axis plane defined; and the method further comprises digitally modifying, by the computing device, the first orientation measurement or the second orientation measurement by applying a rotation based on the heading rotation value computed.

With the present method, the computing device is capable of correcting errors in heading estimates when the two IMUs are arranged on body members in which the joint connecting them has one or two DOF, i.e. degrees of freedom.

When the joint has or substantially has one DOF (the latter meaning that there can be two or three DOF, yet the movement components resulting in the second and/or third DOF are usually minimal and, therefore, can be disregarded considering the reduced amount of error that they may imply), the joint can be regarded as a hinge joint; for example, the knee is a 1-DOF joint since components of knee abduction and rotation are minimal. A 2-DOF joint is, for example, the elbow, which allows extension/flexion and supination/pronation movements.

The existence of soft tissue artifacts or IMU misplacement can be regarded as an additional DOF of a 1-DOF joint, thereby turning it into a 2-DOF joint, or as part of an existing DOF of a 2-DOF joint. Accordingly, both types of joints are considered and, thus, modeled as 2-DOF joints, regardless of the body joint itself allowing or substantially allowing movement between the first and second body members on one or two DOF and regardless of any DOF being caused entirely or affected by phenomena relating to the placement of the units on the body and not to the actual joint itself.

As the body members are connected together by means of the joint, one or more biomechanical constraints may exist in accordance with the degrees of freedom that the joint features. In this sense, the computing device determines the heading error and corrects it by digitally modifying the orientation measurement of one of the first and second IMUs based on the biomechanical constraint that vectors describing the direction in which the segments of the concerned body members extend are to be contained within the joint axis plane. This means that the segments of the first and second body members should be contained within a same plane that is the plane of the axis of the joint. It is to be noted that due to the orientation of one or both body members and, thus, the orientation of the segments thereof with respect to the degrees of freedom of the joint that are considered to have minimal movement components, it is foreseen that both segments are not contained in the joint axis plane; however, these orientations result in an error that is usually several times smaller than the heading error that may affect the heading estimates.

The computing device processes the orientation measurements provided by and received from the first and second units in order to at least compute the length direction of the first body member (with a length vector of the segment thereof) and a heading estimate for the second body member from the orientation measurements, a heading error based on the heading estimate, and the heading rotation value(s) for correcting the heading error. The orientation measurements of the units are indicative of the orientation of the body members on which the sensors are arranged, the heading estimates are indicative of the heading of the body members. As it is known in the art, heading estimates correspond to angles around a vertical axis (i.e. global Z), which correspond to orientations projected onto a horizontal plane like e.g. a ground plane, so an orientation component in the vertical axis is disregarded.

The joint axis plane can be defined by means of the orientation measurement provided by the second unit. A local axis of the second unit can be used for the definition of the joint axis plane because the orientation of the unit can be related to the axis of the joint. The local axis defines the plane in the form of the normal of the plane, which mathematically establishes the plane. As aforementioned, the orientation measurement of the first unit should be contained in the joint axis plane owing to the biomechanical constraint, and the heading deviations of the orientation measurement that make the orientation measurement not to be coplanar with the plane are the heading error that is to be corrected. The heading error is mathematically calculable and, according to the value of the heading error, the computing device computes a heading rotation value that adjusts the heading of the orientation measurement; this means that the vertical component is not altered, something that is important for establishing the movement sequence of the person precisely.

Based on the heading rotation value, the computing device is capable of reducing the heading error by digitally rotating the orientation measurement(s) of one of the units. In this sense, the rotation can be applied to measurements of any one of the first and second units, that is to say, it is not necessary to correct the heading error on the orientation measurement(s) of the first unit and which have been used to determine the heading error and the heading rotation value in the first place. The digital modification of the orientation measurement ensures that the first and second orientation measurements are in a same reference frame, therefore enabling angle measurements of the joint that are used in the provision of the movement sequence. In this sense, the reference frame of the measurements oftentimes will not be aligned with Earth's frame, but that is not necessary for performing angle measurements of the joint.

The arrangement of the IMUs in the first and second body members can be done according to a predetermined unit arrangement, which sets on which body members the IMUs are to be arranged for properly determining the movement sequence of the person or at least the tracked body members thereof. A predetermined unit arrangement preferably also sets where on the body members the IMUs are to be arranged on, and/or it preferably also sets with which orientation the IMUs are to be arranged on. One or more predetermined unit arrangements (a plurality of such arrangements is since each arrangement is suitable for tracking one or more movements to be performed by the person) may be stored in at least one memory of the computing device together, and may be presented with presenting means (e.g. a screen, audio output means such as loudspeakers, a vibrating device, etc.) to the person so that proper arrangement or rearrangement (when the physical exercise to be performed changes) of the IMUs can be effected, in terms of body members and, preferably, position and/or orientation. In some embodiments, the presenting means are part of the motion tracking system whereas, in some other embodiments, the presenting means are not part of the motion tracking system, yet the computing device is connected with the presenting means so as to transmit data thereto.

In the present disclosure, as it is readily apparent from the description, for the purposes of containment or coplanarity of the orientation measurements described, the concerned orientation measurement can be regarded as a free vector (which is translatable in space) or, alternatively, the concerned orientation measurement is a vector that is contained within the joint axis plane irrespective of whether it is contained in said plane or a plane parallel to the joint axis plane.

In the context of the present disclosure, the terms "unit" and "IMU" are used interchangeably to refer to inertial measurement units of the motion tracking system. Further, the term "segment" refers to a segment whose endpoints are the ends of the concerned body member and, thus, is indicative of the direction along which the concerned body member extends.

In some embodiments, the step of digitally processing comprises:

providing a first vector (a, b, c) based on the second orientation measurement;

providing value $z_{orig}$ based on the first orientation measurement; and solving the following system of three equations:

$$ax+by+cz=0,$$

$$y=\sqrt{1-z^2-x^2}, \text{ and}$$

$$z=z_{orig} \text{ and}$$

the heading rotation value is based on a solution to the system of three equations.

As the segment of the second body member is contained in the joint axis plane, the first vector corresponds to a transverse direction of the segment as said vector can serve as the normal vector for the definition of the plane. The definition of the plane relies on the plane equation $ax+by+cz=0$.

By way of example, the digital processing of the computing device is such that it defines said joint axis plane, and provides a second vector ($x_{orig}$, $y_{orig}$, $z_{orig}$) based on the first orientation measurement (thereby providing $z_{orig}$) and a third vector (x, y, z) for computing a heading rotation value. By solving the system of equations (which is defined based on the plane, the magnitude of unit vectors, and the fact that only heading is to be modified) for the third vector, for example the following resulting vector ($x_1$, $y_1$, $z_{orig}$) is obtained, with the values $x_1$ and $y_1$ being obtained from a solution of the system, such as:

$$x_1 = \frac{-acz_{orig} + b\sqrt{-a^2 z_{orig}^2 + a^2 - b^2 z_{orig}^2 + b^2 - c^2 z_{orig}^2}}{a^2 + b^2}, \text{ and}$$

$$y_1 = -\frac{ax_1 + cz_{orig}}{b}.$$

Also, following the same example or another example, the computing device provides a fourth vector (x, y, z) for computing a heading rotation value. Again, by solving the system of equations but for the fourth vector, for example the following resulting vector ($x_2$, $y_2$, $z_{orig}$) is obtained, with the values $x_2$ and $y_2$ being obtained from a solution of the system, such as:

$$x_2 = -\frac{acz_{orig} + b\sqrt{-a^2 z_{orig}^2 + a^2 - b^2 z_{orig}^2 + b^2 - c^2 z_{orig}^2}}{a^2 + b^2}, \text{ and}$$

$$y_2 = -\frac{ax_2 + cz_{orig}}{b}.$$

The third vector could take the solution according to any one of $x_1$ and $x_2$, and the respective value of y.

In some embodiments, the heading rotation value comprises a difference between the solution to the system of three equations and the orientation measurement to which the rotation is to be applied in the step of digitally modifying.

The heading rotation value is the rotation that compensates the heading error of the orientation measurement that is digitally modified. Accordingly, the heading rotation value may be the angle that cancels out either a difference between the first orientation measurement and the solution (e.g. one of the third and fourth vectors of the aforementioned example), or a difference between the second orientation measurements and the solution (e.g. one of the third and fourth vectors).

In some other embodiments, the heading rotation value comprises a combination of the solution to the system of three equations with one or more heading rotation values computed for previous orientation measurements provided by the first and second units.

The rotation applied to the orientation measurement in the digital modification step takes into account previous rotation values so that the correction of the heading error does not solely rely on the heading error computed for the current measurements provided by the first and second units. Hence, the heading rotation value results from an integration of:

a) the angle that cancels out either a difference between the first orientation measurement and the solution to the system (e.g. one of the third and fourth vectors of the aforementioned example) or a difference between the second orientation measurements and the solution (e.g. one of the third and fourth vectors), and b) one or more previous heading rotation values;

with the integration of a) and b) above, the rotation applied takes into account preceding heading error corrections, in this way sporadic errors in the orientations measured by the units do not affect the modified orientation in a large degree.

In some embodiments, the step of digitally processing further comprises selecting the solution to the system of three equations that at least one of: fulfills one or more predetermined biomechanical constraints, and results in an instantaneous heading error that: is determined not to be excessive by the computing device, and/or is less than an instantaneous heading error for the other solution to the system of three equations. Further, in these embodiments, the heading rotation value is based on the selected solution to the system of three equations.

When the computing device computes more than one solution to the system of three equations, it selects the solution that results in a rotated orientation measurement deemed more realistic for the first and second body members and the common joint thereof. Accordingly, either one of the solutions may be positively selected, meaning that the solution meets certain positive criterion or criteria (i.e. fulfillment of one or more predetermined biomechanical constraints and/or not excessive instantaneous heading error and/or smaller instantaneous heading error), or one of the solutions may be discarded because it meets certain negative criterion or criteria (i.e. non-fulfillment of one or more predetermined biomechanical constraints and/or excessive instantaneous heading error and/or greater instantaneous heading error). The computing device is to select the solution that does not result in a rotation of the (first or second) orientation measurement that yields a joint movement that is considered as being impossible and/or results in a rotation that could only be possible if the dynamics of the heading error are too fast, however said dynamics are expected to be slow and accumulate over time.

In some of these and in some other embodiments, if the system of equations does not yield any solution due to the provided vectors resulting in a system with no real solutions or, alternatively, if disambiguation of the two solutions by the positive or negative criteria is not possible, the computing device either applies a rotation according to a previously computed heading rotation value or a heading rotation value resulting from an integration (which is either a combination of items a) and b) as explained above, or a combination of a plurality of previous heading rotation values according to item b) above), or no rotation is applied to the first or second orientation measurement. In these cases, the rotation(s) may be applied to the orientation measurements provided by the units in previous and/or posterior moments during the motion tracking procedure.

In some embodiments, the method further comprises digitally providing, by the computing device, a movement sequence of the person based on the orientation measurements provided by the first and second units wherein at least some orientation measurements of one the first and second units have been digitally modified.

Owing to the digital modification for correcting the heading error, meaningful angle measurements of the joint can be made possible even when non-negligible heading errors exist, e.g. heading errors greater than 10°. Additionally, the movement sequence provided is more accurate than a movement sequence provided with no digital modification of the at least some orientation measurements.

In some embodiments, the method further comprises repeating at least the digital steps one or more times with most recent orientation measurements provided by the first and second units for correction of heading error in the measurements provided by the units.

The repetition of the digital steps with the different orientation measurements provided by the units enables both the determination and correction of the heading errors during the motion tracking procedure, for instance while the person is physically exercising for rehabilitation purposes. Preferably, the steps are repeated during the entire motion tracking of the person and each time the first and second units keep provide new orientation measurements.

In some embodiments, the rotation applied in the step of digitally modifying is at least further based on one or more heading rotation values previously computed for digital modification of previous orientation measurements.

In some embodiments, the method further comprises, prior to the step of digitally processing, arranging the first and second units on the first and second body members of the person, respectively.

In some embodiments, the method further comprises calibrating the first and second units after arranging them on the first and second body members.

The calibration, which can be made in accordance with any calibration procedure known in the art for inertial measurement units, assists in reducing the heading error due to errors in the reference of the sensing devices of the units and determining the placement and/or orientation of the units on the body members for the computing device to establish length directions of the body members or, in other words, establish the segments of the body members. The calibration procedure, which may be triggered by the computing device before starting the motion tracking procedure, involves movement of the first and second body members.

In some embodiments, the method further comprises calibrating the first and second units prior to arranging them on the first and second body members.

The calibration, which can be made in accordance with any calibration procedure known in the art for inertial measurement units, assists in reducing the heading error due to errors in the reference of the sensing devices of the units. Also, as the units provided accurate and calibrated orientation measurements right after the calibration, the computing device is capable of determining the orientations of the units upon arrangement of the same on the person.

In some embodiments, at least the second unit is arranged on the second body member such that one of three axes of the second unit is aligned or substantially aligned with a segment of the second body member. Preferably, the first unit is on the first body member such that one of three axes of the first unit is aligned or substantially aligned with a segment of the first body member.

Aligned or substantially aligned arrangement can be attained with attaching devices or means for units that assist in orienting the units or force certain orientation or orientations of the units. To this end, the attaching devices or means may comprise straps, Velcro, etc. with visual indications regarding how the unit is to be attached thereto, and/or include a casing on the strap, Velcro, etc. that is adapted to receive the unit with a predetermined orientation. Said casing, which may be formed of a single member or a plurality of members, comprises a geometry that cooperates with a geometry of the unit for forcing a predetermined orientation of the unit. Likewise, the attaching devices or means may be part of the units such that the unit with sensing devices is mechanically coupled with the strap, Velcro, etc. and, thus, is not releasable therefrom.

Also, it is envisaged that the person may properly arrange the units on the body members without requiring any guidance or assistance from casings or visual indications in the attaching devices or means. In this sense, presenting means that provide instructions to the user for the motion tracking procedure preferably provide instructions to the user for arranging the units.

In addition to the above, further means for assisting or enforcing the proper arrangement of the units known in the art are also possible.

In some embodiments, the first and second body members respectively are an upper arm and a forearm or vice versa, or the first and second body members respectively are a thigh and a shank or vice versa.

In some embodiments, further comprising providing, by each of the first and second units, the orientation measurements to be digitally processed.

In some embodiments, each of the first and second units further comprises a magnetometer.

A second aspect of the invention relates to a motion tracking system comprising:

a computing device comprising at least one processor and at least one memory; and first and second inertial measurement units adapted to be arranged on first and second body members of a person and each at least comprising an accelerometer and a gyroscope;

the at least one processor is configured, together with the at least one memory, to carry out a method according to the first aspect of the invention.

With the motion tracking system, motion of a person or of the body members with units arranged thereon can be tracked such that heading errors in the orientation measurements can be corrected.

The motion tracking system can provide a movement sequence of the person or the body members, and assess the movements and physical exercises performed by the person without requiring calibration of the units (which, typically, is a cumbersome process that may even require some skill from the user to be correctly performed) and/or mapping of magnetic disturbances before and/or during the motion tracking procedure.

Accordingly, the motion tracking system is capable of correcting heading errors during the motion tracking procedure itself, thereby improving both the quality of the resulting movement sequence provided and the user experience, reducing the setup time of the motion tracking system and, additionally, lowering the skill necessary from the person to use the motion tracking system. Concerning the latter, it is to be noted that oftentimes the user is a person with little knowledge of technology and complex and not so complex manipulation of the motion tracking system becomes a hurdle for this type of users.

In some embodiments, each of the first and second units further comprises a magnetometer.

In some embodiments, the motion tracking system further comprises attaching devices or means for the first and second units, or each of the first and second units comprises attaching devices or means. In some of these embodiments, the attaching devices or means comprise a casing adapted to receive a respective unit with a predetermined orientation. In some other embodiments, the attaching devices or means and the respective unit are mechanically coupled.

A third aspect of the invention relates to a computer program product that has instructions which, when executed by a computing device of a motion tracking system comprising first and second inertial measurement units adapted to be arranged on first and second body members of a person and each at least comprising an accelerometer and a gyroscope, cause the computing device to perform a method according to the first aspect of the invention.

Upon running the computer program product on one or more processors of the computing device, the motion tracking system both determines whether heading errors exist in the measurements of the IMUs and modifies them based on the determined heading errors for correction thereof.

In some embodiments, the computer program product is embodied on a non-transitory computer readable medium.

A fourth aspect of the invention relates to a data stream which is representative of a computer program product according to the third aspect of the invention.

Same advantages as those described for the first aspect of the invention also apply to the second, third and fourth aspects of the invention.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention, but just as examples of how the invention can be carried out. The drawings comprise the following figures.

DESCRIPTION OF WAYS OF CARRYING OUT THE INVENTION

Figure 1A:
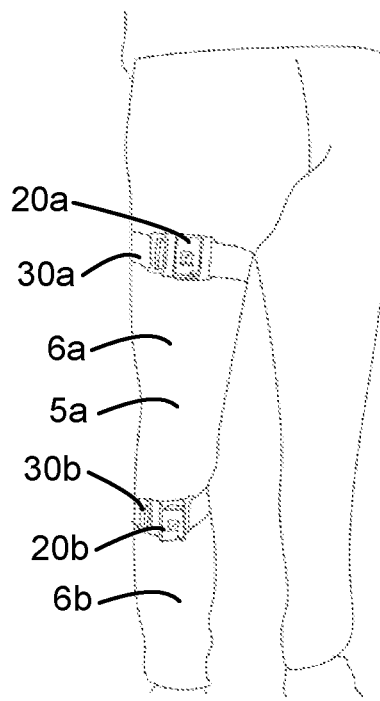
FIGS. 1A to 1C show a person with IMUs of a motion tracking system arranged on a leg thereof for explanation of possible deviations in heading estimates or heading errors that could be compensated for with methods and system in accordance with the present disclosure.
Figure 1B:
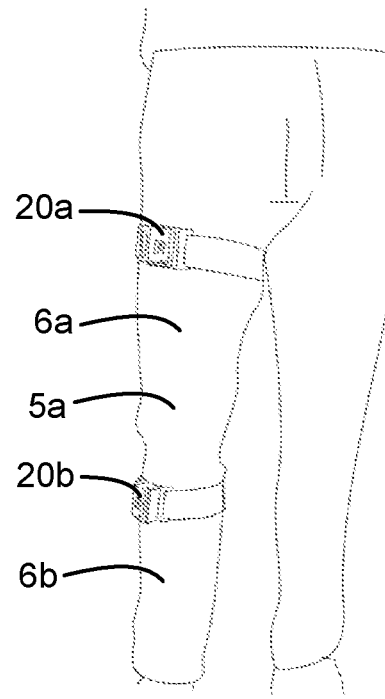
Figure 1C:
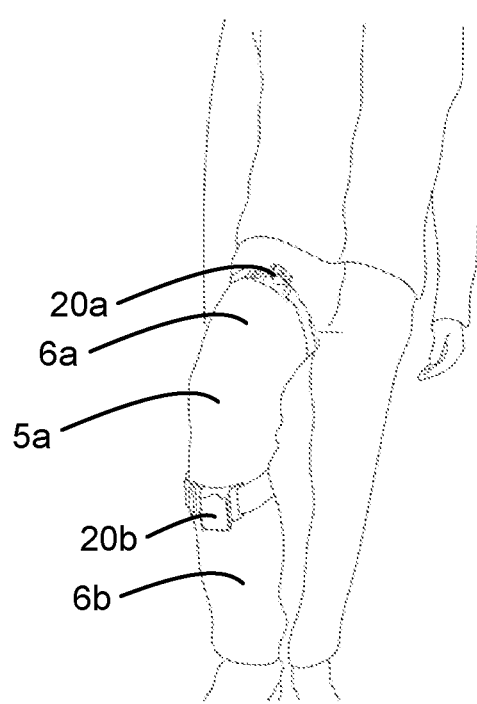

FIGS. 1A to 1C show a person 1 with first and second IMUs 20a, 20b of a motion tracking system (e.g. the system 10 of FIG. 2 below) arranged on a leg according to a predetermined unit arrangement.

In this embodiment, the first IMU 20a is arranged on the thigh 6a, and the second IMU 20b is arranged on the shank 6b of the same leg. The thigh 6a and the shank 6b are connected by the knee 5a; the thigh 6a and the shank 6b each moves one relative to the other only around the axis of the knee 5a as a 1-DOF joint. In some other embodiments, the first IMU 20a is arranged on the shank 6b and the second IMU 20b is arranged on the thigh 6a. The first and second IMUs 20a, 20b are arranged on these body members 6a, 6b owing to first and second straps 30a, 30b even though other attaching means or devices for arranging the IMUs 20a, 20b on the person 1 are also possible.

In FIG. 1A, the person 1 is standing still and has both IMUs 20a, 20b arranged thereon such that they are aligned with the segments of the thigh 6a and the shank 6b; it is noted that the segments define a length of a respective body member 6a, 6b. In this situation, errors in the heading estimates that are computed by the computing device can exist due to cumulated errors in the sensing devices of the IMUs 20a, 20b that influence the measurements provided, and/or due to magnetic disturbances. However, there are no deviations in the heading estimates due to soft tissue artifacts or due to misplacement of the units 20a, 20b.

From the standing still position, the person 1 performs a hip external rotation as illustrated in FIG. 1B. The second IMU 20b rotates in accordance with the rotation of the hip and is aligned with the direction in which the foot of the person 1 is pointing. The first IMU 20a also rotates in accordance with the rotation of the hip, but due to the soft tissues of the thigh 6a, the rotation undergone by the first IMU 20a is dampened, thereby causing the IMU 20a not to rotate as much as the rotation of the hip and the second IMU 20b. It can be appreciated that the segments of the thigh 6a and the shank 6b remain aligned owing to the hinge joint that is the knee 5a, but the IMUs 20a, 20b do not remain aligned in contrast to the situation of FIG. 1A.

Turning to FIG. 1C, the person 1 performs a hip flexion movement from the standing still position of FIG. 1A. Again, due to the soft tissues of the thigh 6a, the first and second IMUs 20a, 20b are not aligned yet the segments of these body members 6a, 6b are. In this case, the first IMU 20a rotates inwardly as a result of the soft tissue artifacts whereas the second IMU 20b does not. Typically, soft tissue problems are more prevalent around the segment than in other directions.

As it can be appreciated from the above examples, the heading estimates of the joint axis (knee axis in these examples) given by each of the first and second units 20a, 20b should be the same when no heading errors exist (the measurements of the sensing devices are error-free and tolerances of the sensing devices are disregarded), but in FIGS. 1B and 1C the heading estimates are not the same (even without said heading errors) because there are deviations caused by the soft tissue artifacts. In fact, full orientation estimates (i.e. orientation estimates in the three dimensions) of the joint axis should be the same, so correction in the vertical direction would also have to be effected should the vertical reference not be reliable, but it has been found out that accelerometers of IMUs 20a, 20b do provide a vertical reference that is both accurate and reliable. Therefore, it is considered that only the heading errors need be corrected. Correction of heading errors is complex because soft tissues, IMU misplacement and/or supination/pronation movements mask heading errors in the measurements of the sensing devices.

Methods and systems according to the present disclosure make possible to correct heading errors, and in the following cases too, which are considered and, therefore, modelled as an additional degree of freedom in the movement of one of the body members:
 there are soft tissue artifacts (as in the above examples);
 there is supination/pronation of the forearm; and/or
 one of the units is misplaced.

Figure 2:
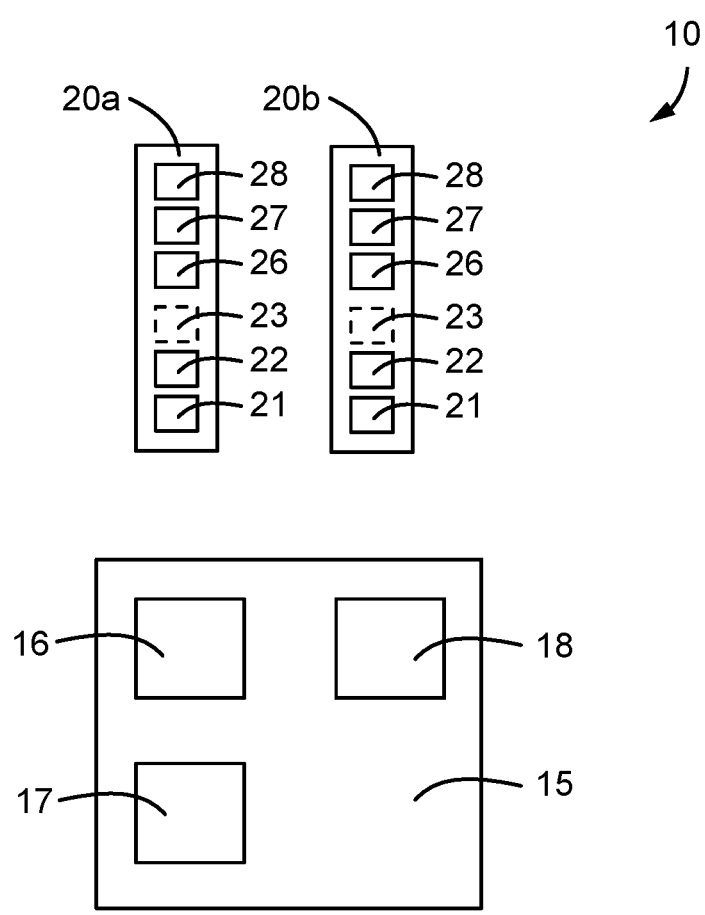
FIG. 2 diagrammatically shows a motion tracking system in accordance with an embodiment.

FIG. 2 diagrammatically shows a motion tracking system 10 in accordance with an embodiment. The motion tracking system 10 includes first and second inertial measurement units 20a, 20b, and a computing device 15.

Each IMU 20a, 20b at least includes two sensing devices: an accelerometer 21, and a gyroscope 22. As shown with dashed lines, in some embodiments each of the IMUs 20a, 20b further includes a magnetometer 23.

The first and second IMUs 20a, 20b further include at least one processor 26, at least one memory 27, and a first communications module 28 for transmitting and receiving data that enables the IMUs to transmit (through a wired or wireless communications technology and protocol known by a skilled person, for instance but without limitation, Bluetooth communications, cellular network communications such as GSM, UMTS or LTE, wireless LAN communications, etc.) measurements of the sensing device(s) 21-23 to the computing device 15. The same first communications modules 28 enable the units 20a, 20b to receive data from the computing device 15.

In some preferred embodiments, the at least one processor 26 of the IMUs 20a, 20b runs a sensor fusion algorithm for processing the measurements of the sensing devices 21-23 within the respective IMU. The sensor fusion algorithm is intended to enhance the raw measurements of the sensing devices by correcting errors thereof due to drifts of the sensing devices and, thus, outputs processed measurements that are to be transmitted to the computing device 15. By way of example, biases of the gyroscopes 22 accumulate over time and worsen the accuracy of the measurements of the IMUs 20a, 20b, and magnetic disturbances also bias the measurements of the magnetometers 23 when the IMUs 20a, 20b comprise said sensing device. The sensor fusion algorithm may reduce the influence of these biases with the measurements provided by remaining sensing device(s), but may not completely cancel these biases out.

The computing device 15 includes at least one processor 16, at least one memory 17, and a second communications module 18 for transmitting and receiving data (through a wired or wireless communications technology and protocol known by a skilled person, for instance but without limitation, Bluetooth communications, cellular network communications such as GSM, UMTS or LTE, wireless LAN communications, etc.).

Figures 3A, 3B:
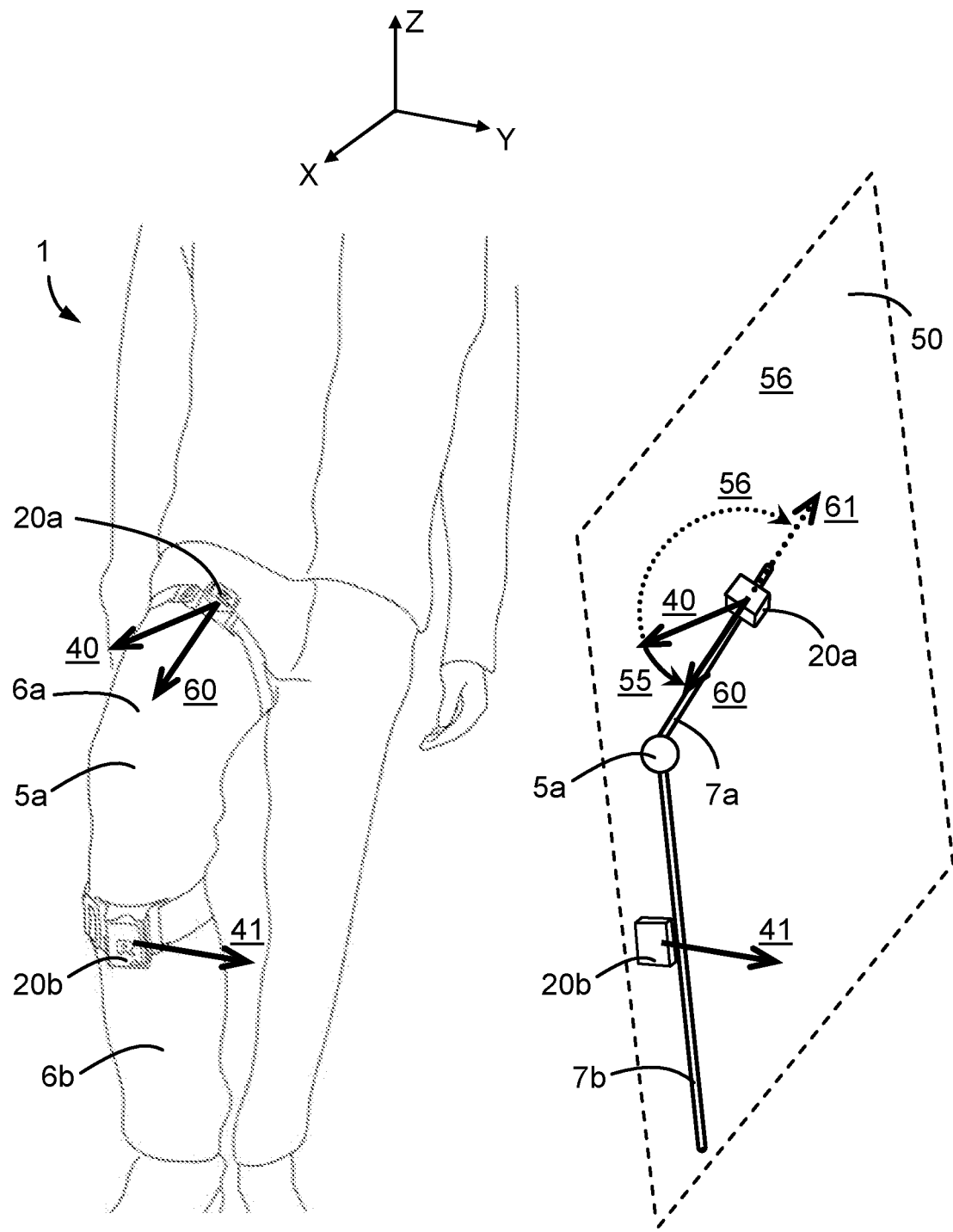
FIGS. 3A, 4A and 4C show a person with IMUs of a motion tracking system, one of which includes a heading error, whereas FIGS. 3B, 4B and 4D illustratively represent the tracked segments of FIGS. 3A, 4B and 4D, respectively, and possible heading error corrections.

FIG. 3A shows the person 1 with first and second IMUs 20a, 20b of a motion tracking system (e.g. the system 10 of FIG. 2) on the thigh 6a and the shank 6b, respectively, and FIG. 3B illustratively represents depicted segments 7a, 7b corresponding to the length of the thigh 6a and the shank 6b with the orientations of FIG. 3A, together with a joint axis plane 50 and the IMUs 20a, 20b.

The person 1 is performing a hip flexion. The first and second IMUs 20a, 20b provide respective orientation measurements such as first orientation measurement 40 and second orientation measurement 41.

The computing device (e.g. the computing device 15) of the motion tracking system receives the orientation measurements 40, 41 from the IMUs 20a, 20b and digitally processes them for determining whether heading errors are present in the orientation measurements 40, 41 and correcting the same.

To this end, the computing device processes the second orientation measurement 41 to establish the local axes of the second unit 20b and, based on these local axes and whose orientations can be obtained in global coordinates, define a joint axis plane 50 corresponding to the plane of the axis of the knee 5a. In this case, one of the local axes of the second unit 20b is used as a normal vector, e.g. (a, b, c) of the plane 50, which is sufficient to define it by equation: $ax+by+cz=0$.

In some embodiments, none of the local axes of the second unit 20b coincides with the axis of the knee 5a, for instance when the second unit 20b is misplaced on the shank 6b. In such situations, the computing device is to calibrate the units 20a, 20b by way of a calibration procedure for determining the placement of the units 20a, 20b on the body members 6a, 6b, and then a vector is provided by the computing device to define the joint axis plane 50; said vector does not coincide with the local axes of the second unit 20b but is based on the actual orientation of the (misplaced) second unit 20b. The calibration procedure triggered once the units 20a, 20b are arranged on the person 1 can be a calibration procedure of the state of the art whereby either the person 1 is requested to perform predetermined movement(s) for calibration purposes that involve motion of the body members with units 20a, 20b arranged thereon, and/or the units 20a, 20b have their sensing devices calibrated such that the headings of the measurements thereof are accurate at least for a certain amount of time, e.g. one minute, two minutes, five minutes, etc., without requiring any predetermined movement(s) from the person 1. By way of example, a calibration procedure of the state of the art is that described in PCT/PT2018/050044, which is incorporated by reference in its entirety herein.

The computing device computes a vector corresponding to a length direction of the segment 7a of the thigh 6a based on the first orientation measurement 40, for example said first orientation measurement 40 can be defined by vector ($x_{orig}$, $y_{orig}$, $z_{orig}$). The computing device then determines that there is a heading error because the first orientation measurement 40 is not coplanar with the plane 50 defined by the computing device due to accumulated bias in the gyroscope and/or magnetic distortions affecting the magnetometer (if any) of the IMU; the orientation measurement 40 should be coplanar owing to the biomechanical constraints of the knee 5a.

The soft tissue artifacts do not change the orientation in the length direction of the thigh 6a (i.e. that of the segment 7a) but change those in the other two directions, namely the directions around the length direction, hence the orientation in the length direction is used in the correction of the heading error. The computing device computes how the orientation measurement 40 is to be rotated so that it ends up being coplanar with the joint axis plane 50. The computing device thus computes heading rotation(s) 55, 56 (e.g. angles, quaternions) whereby the orientation measurement 40 becomes coplanar with the joint axis plane 50, thereby providing first and second coplanar orientations 60, 61. The heading rotation(s) 55, 56 correspond to the heading error computed with inverse sign. For the sake of clarity only, a first heading rotation 55 is shown with solid line as an angle for providing the first coplanar orientation 60 also shown with solid line, whereas a second heading rotation 56 is shown with dashed line as an angle for providing the second coplanar orientation 61 also shown with dashed line. The heading rotations 55, 56 are obtained by digitally solving a system of three equations:

$$ax+by+cz=0,$$

$$y=\sqrt{1-z^2-x^2}, \text{ and}$$

$$z=z_{orig}.$$

In this regard, the first coplanar orientation 60 can be defined by vector ($x_1$, $y_1$, $z_{orig}$) and, accordingly, a first heading rotation value can be computed so that $x_{orig}$ and $y_{orig}$ become $x_1$ and $y_1$, respectively, thus the heading rotation value 55 is such that $$x_1 = -\frac{-acz_{orig} + b\sqrt{-a^2 z_{orig}^2 + a^2 - b^2 z_{orig}^2 + b^2 - c^2 z_{orig}^2}}{a^2+b^2} \text{ and}$$

$$y_1 = -\frac{ax_1 + cz_{orig}}{b}.$$

Likewise, the second coplanar orientation 61 can be defined by vector $(x_2, y_2, z_{orig})$ and, accordingly, the second heading rotation value can be computed so that $x_{orig}$ and $y_{orig}$ become $x_2$ and $y_2$, respectively, thus the heading rotation value is such that $$x_2 = -\frac{acz_{orig} + b\sqrt{-a^2 z_{orig}^2 + a^2 - b^2 z_{orig}^2 + b^2 - c^2 z_{orig}^2}}{a^2 + b^2} \text{ and}$$

$$y_2 = -\frac{ax_2 + cz_{orig}}{b}.$$

The definition of the vertical component of the vectors as $z_{orig}$, which is a value from the vector of the first orientation measurement 40, is due to the fact that heading is to be corrected by means of a rotation around the global vertical axis (i.e. Z axis illustrated), thus the vertical component is disregarded. As it can be appreciated, in some other examples, the first coplanar orientation 60 is defined by vector $(x_2, y_2, z_{orig})$ and the second coplanar orientation 61 is defined by vector $(x_1, y_1, z_{orig})$.

The computing device establishes that the first coplanar orientation 60 is the correct orientation out of the two orientations 60, 61 since it is the orientation that:
  fulfills one or more predetermined biomechanical constraints established for the concerned joint, and/or
  a difference between the computed heading error and a previously computed heading error fulfills one or both of:
    is smaller than the difference between the computed heading error for the other orientation and a previously computed heading error, and
    does not exceed a predetermined heading error threshold, namely the difference shall not exceed a threshold of e.g. 10°, 20°, etc.

In relation to the fulfillment of predetermined biomechanical constraints, for example the second coplanar orientation 61 results in a movement of the joint that is deemed impossible (e.g. knee hyperextension) or is caused by a soft tissue artifact deemed excessive for the concerned body member.

By way of example, when the IMUs 20a, 20b are arranged on the leg of the person 1, it has been found out that soft tissue artifacts should not result in a difference of more than 45° around the direction of the segment (i.e. length direction of the body member), and the solution being closer to the joint axis plane is the one deemed correct; positive Y axis is typically closer to the joint axis than negative Y axis, therefore, in these cases, the heading rotation value that is selected is that of positive Y of the thigh 6a joint axis, which is closer to the positive Y of the shank 6b.

Figure 4A:
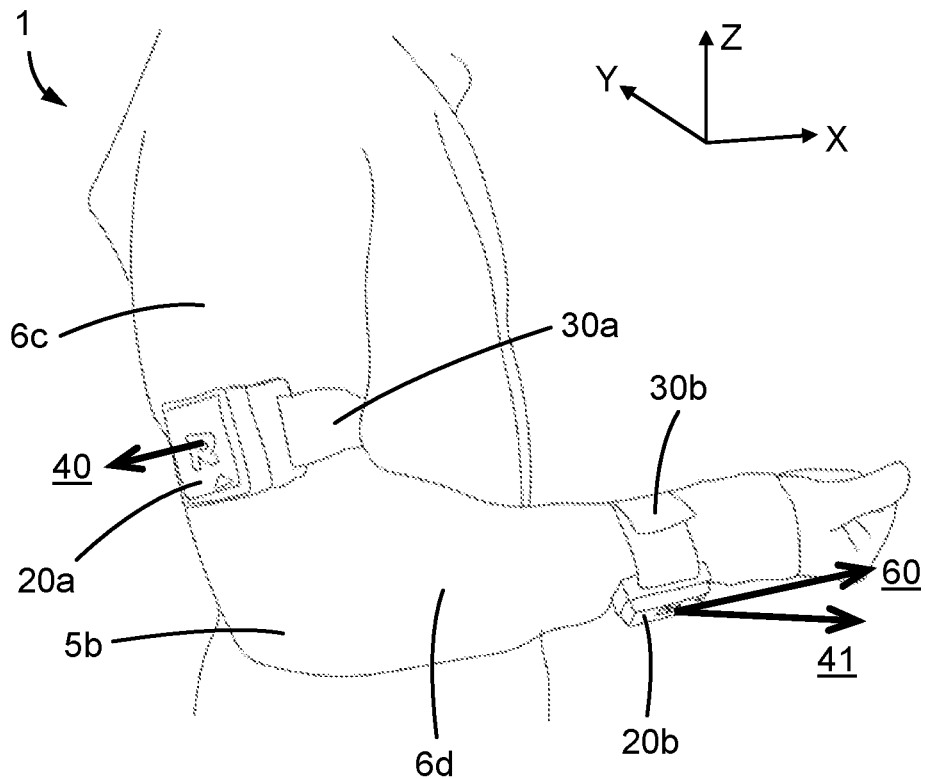
Figure 4B:
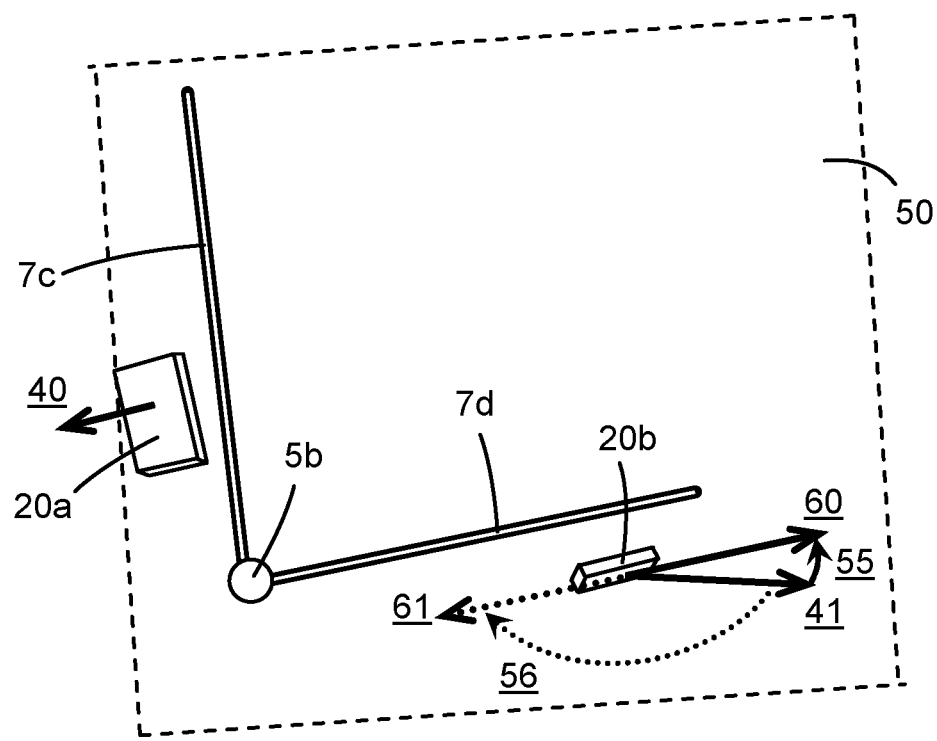
Figure 4C:
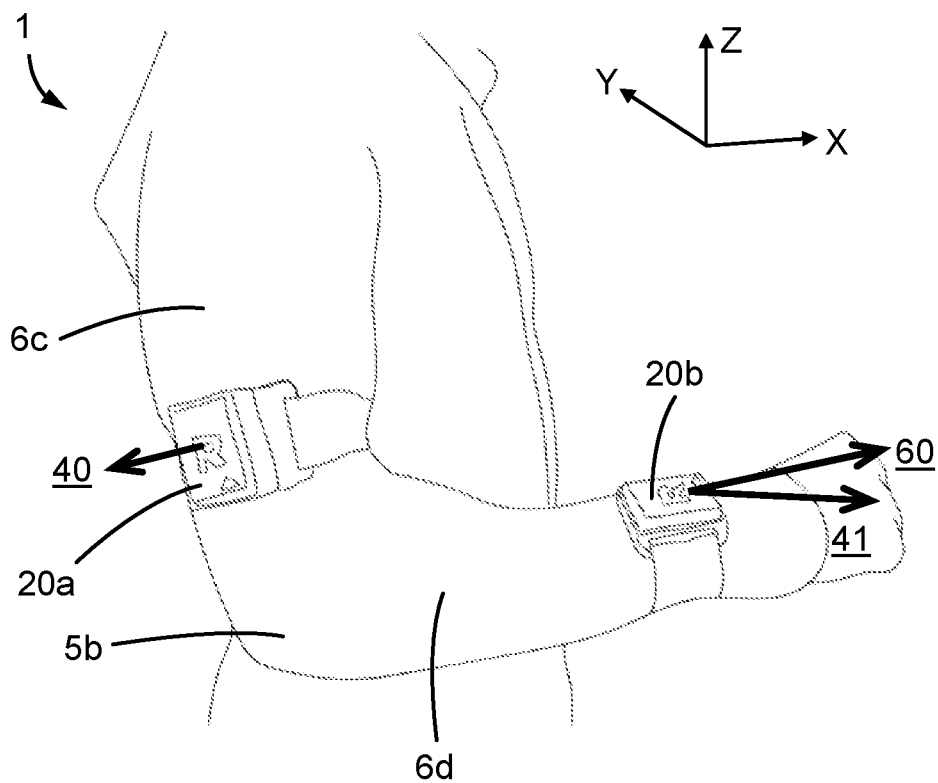
Figure 4D:
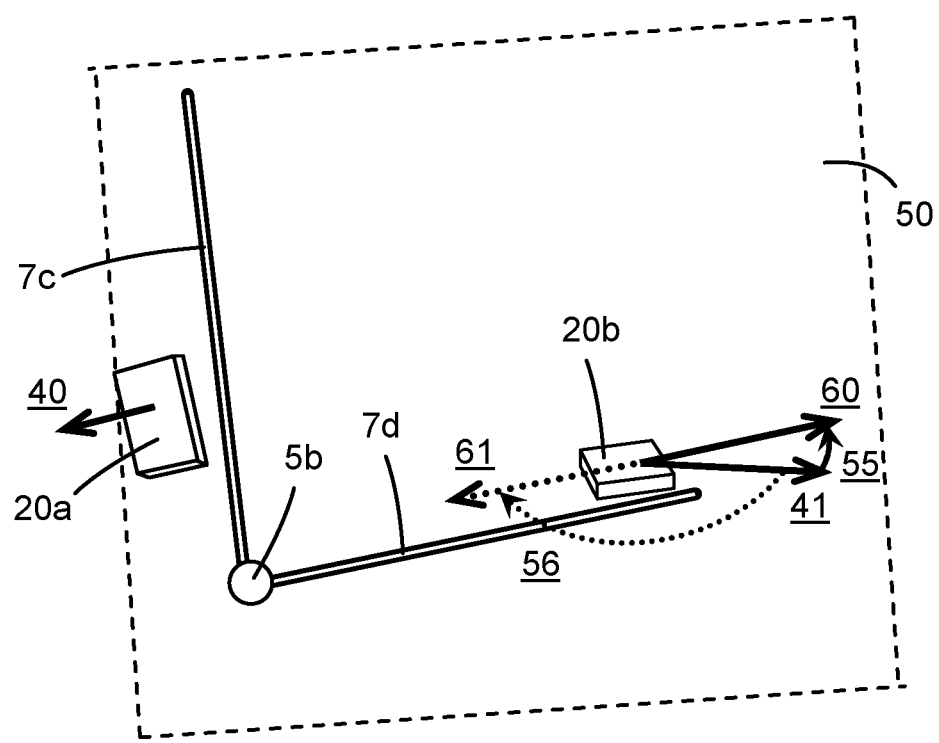

FIGS. 4A and 4C show the person 1 with first and second IMUs 20a, 20b of a motion tracking system (e.g. the system 10 of FIG. 2) on the forearm 6d and the upper arm 6c, respectively, and FIG. 4B and 4D illustratively represent depicted segments 7d, 7c corresponding to the length of the forearm 6d and the upper arm 6c with the orientations of FIGS. 4A and 4C, together with a joint axis plane 50 and the IMUs 20a, 20b.

The person 1 is performing forearm pronation as illustrated with FIGS. 4A and 4C. The first and second IMUs 20a, 20b provide respective orientation measurements such as first orientation measurement 40 and second orientation measurement 41.

The computing device (e.g. the computing device 15) of the motion tracking system receives the orientation measurements 40, 41 from the IMUs 20a, 20b and digitally processes them for determining whether heading errors are present in the orientation measurements 40, 41 and correcting the same.

With a digital processing as described in the present disclosure, in this example, the computing device processes the first orientation measurement 40 and provides a vector corresponding to a local axis of the first IMU 20a to define the axis plane 50 of the joint 5b, in this case the elbow 5b of the person 1.

The computing device solves the system of equations for a vector provided based on the second orientation measurement 41, and with the solutions it computes heading rotations 55, 56 for making the second orientation measurement 41 to be contained within the joint axis plane 50. One of the solutions can be selected over the other according to any one of the criteria described in relation to FIGS. 3A-3B.

It is noted that the vectors described for instance with reference to FIGS. 3A-3B and 4A-4D are either free vectors, from which those of the first and second planar orientations 60, 61 are to be contained in the joint axis plane 50. Alternatively, the vectors described are not free vectors but are to be contained in the joint axis plane 50 or a plane parallel thereto.

Albeit in the embodiments of FIGS. 3A-3B and FIGS. 4A-4D it has been described that the rotation of the orientation measurements is applied to the first and second orientation measurements 40, 41, respectively, in some other embodiments the rotation is applied to the second and first orientation measurements 41, 40, respectively. That is to say, the rotation is applied to the orientation measurement used for defining the joint axis plane 50, in which case the rotation to be applied is the same as if it were to be applied to the first and second orientation measurements 40, 41 as explained in relation to FIGS. 3A-3B, and 4A-4D, respectively, but with inverse sign.

Figure 5:
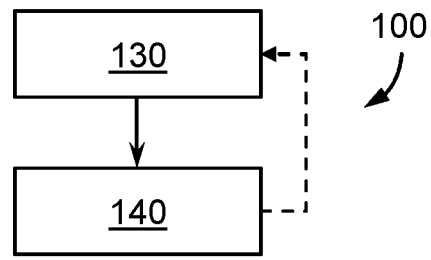
FIGS. 5 and 6 diagrammatically show methods in accordance with embodiments.

FIG. 5 diagrammatically shows a method 100 in accordance with embodiments.

The method 100 comprises a step 130 whereby a computing device (e.g. the computing device 15 of FIG. 2) of a motion tracking system (e.g. the system 10 of FIG. 2) digitally processes orientation measurements provided by each of first and second inertial measurement units (e.g. the IMUs 20a, 20b of FIGS. 1A-1C, 2, 3A-3B, 4A-4D, with or without magnetometers 23) of a motion tracking system that are arranged on first and second body members (e.g. thigh and shank, upper arm and forearm) of a person, respectively, according to a predetermined unit arrangement. The orientation measurements are processed in such a way that a heading error is computed from a heading estimate of one or more measurements of one of the first and second IMUs, and a heading rotation value is also computed based on the heading error so that the heading error may be corrected. Such digital processing may be, for example, as described above in relation to the example of FIGS. 3A and 3B.

The orientation measurements that the computing device processes may be raw measurements, i.e. values measured by a sensing device of a respective unit, or processed measurements, i.e. values modified by the processor(s) of the IMU, for instance owing to a sensor fusion algorithm that is intended to improve the measurements of the IMU by combining the measurements of the different sensing devices.

The method 100 further comprises a step 140 whereby the computing device digitally modifies one or more measurements of one of the first and second IMUs for correcting the heading error. This is attained by applying a rotation at least based on a value or values computed in the step 130 in which the computing device digitally processes the measurements.

Preferably, the steps 130 and 140 are carried out in real time or almost in real time as the IMUs provide the measurements, even though, in some embodiments, the heading error correction is performed later on during the motion tracking procedure or after completion of the same. In this sense, the steps 130 and 140 can be carried out during physical exercising of the person, therefore the orientation measurements are provided by the units and the computing device processes and modifies them while the person moves one or both of the first and second body members; movement of the body members comprises linear motion and/or rotation of the respective body member.

In some embodiments, the steps 130 and 140 carried out by the computing device are repeated (as illustrated with a dashed line) a number of times so as to correct heading errors in orientation measurements provided by the IMUs during a motion tracking procedure. Therefore, upon providing more recent measurements, the computing device digitally processes the same and digitally modifies measurements of one of the IMUs so as to correct the heading error, thereby making possible to improve the precision of the movement sequence that is to be provided by the computing device.

In some embodiments, the method 100 further comprises one or more of steps 110, 120 and 150 as described next in relation to method 101 of FIG. 6.

Figure 6:
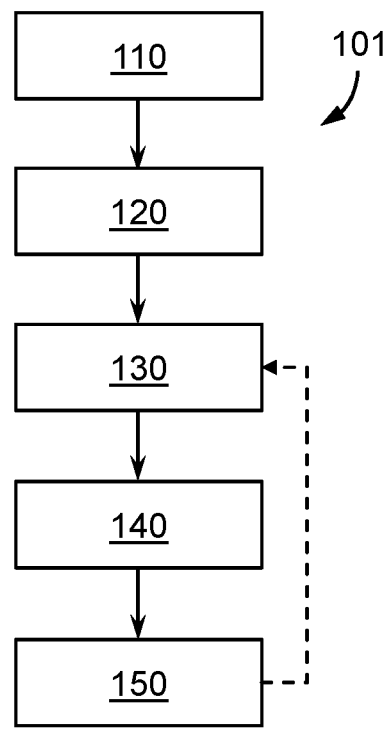

FIG. 6 diagrammatically shows a method 101 in accordance with embodiments.

The method 101 comprises a step 110 whereby the first and second units are arranged on the first and second body members, respectively. The units may be arranged 110 by way of attaching devices or means such as e.g. straps, Velcro, etc.

At least the unit whose orientation measurement(s) is/are used in the definition of the joint axis plane is preferably arranged on the respective body member (preferably the body member of the two body members that only rotates around the joint axis, or mostly rotates around the joint axis) such that a local axis of the unit out of the three local axes is aligned or substantially aligned with the segment of the body member, otherwise a calibration procedure is effected whereby the computing device determines how the IMUs are arranged on the body segments so that the orientation of the IMUs can be specified with respect to the segments of the body members (even if no local axis of one or both units is aligned or substantially aligned with the corresponding segment). More preferably, both units are arranged on the respective body members such that a respective local axis of the units out of the three local axes is aligned or substantially aligned with the segment of the respective body member, or the aforementioned calibration procedure is performed for determining the orientation of the IMUs as indicated.

The method 101 further comprises a step 120 whereby the first and second units, once arranged 110 on the body members of the person, provide the orientation measurements to be digitally processed 130 and modified 140 by the computing device. The orientation measurements may be provided to the computing device via wired or, preferably, wireless communications. The orientation measurements may be raw measurements or processed measurements, e.g. processed with a sensor fusion algorithm as known in the art.

The method 101 further comprises the steps 130, 140 of digitally processing and modifying the orientation measurements provided 120. The method 101 also comprises a step 150 whereby the computing device digitally provides a movement sequence of the person based on the orientation measurements provided by the first and second units, and where at least some (or all) orientation measurements of one the first and second units have been digitally modified 140.

The movement sequence comprises data of the motion tracking procedure that indicates how the person or at least the body members thereof with IMUs have behaved in terms of movements and orientations during said procedure. Thanks to the movement sequence provided 150, the computing device is capable of assessing whether the person has performed movements or physical exercises according to predetermined criteria, for instance for physical rehabilitation purposes. The correction of heading errors present in the orientation measurements enhances the accuracy of the movement sequence and, thus, of any additional evaluation, for example the mentioned movement or physical exercise assessment, which may be carried out according to state of the art procedures known in the art, for example but without limitation, a physical exercise evaluation procedure as described in PCT/EP2019/066237, which is incorporated by reference in its entirety herein.

A motion tracking system (e.g. the system 10 of FIG. 2) according to the present disclosure is adapted to carry out methods such as methods 100, 101 of FIGS. 5 and 6 owing to a computing device (e.g. the computing device 15 of FIG. 2) configured to perform steps 130, 140, 150 (i.e. the at least one processor is configured, together with the at least one memory, to carry out the steps 130, 140, 150).

In this text, the terms first, second, third, etc. have been used herein to describe several devices, elements or parameters, it will be understood that the devices, elements or parameters should not be limited by these terms since the terms are only used to distinguish one device, element or parameter from another. For example, the first orientation measurement could as well be named second orientation measurement, and the second orientation measurement could be named first orientation measurement without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method of compensating for heading errors of a plurality of inertial measurement units, the method comprising:

providing first and second inertial measurement units each comprising an accelerometer and a gyroscope;

arranging the first and second inertial measurement units on first and second body members of a person, the first and second body members being connected by a joint;

obtaining a first orientation measurement of the first unit;

computing a heading rotation value for containing the first orientation measurement within an axis plane of the joint based on a second orientation measurement of the second measurement unit; and modifying the first orientation measurement or the second orientation measurement by applying a rotation based on the heading rotation value computed.

2. The method of claim 1, wherein each of the first and second units further comprises a magnetometer.

3. The method of claim 2, wherein each of the obtained orientation measurements comprise information obtained from the accelerometer, the gyroscope, and the magnetometer of each of the measurement units.

4. The method of claim 1, wherein the step of computing the heading rotation value comprises:

providing a first vector (a, b, c) based on the second orientation measurement;

providing value $Z_{orig}$ based on the first orientation measurement; and solving the following system of three equations:

$ax+by+cz=0$, $y=\sqrt{1-z^2-x^2}$, and $z=z_{orig}$ and the heading rotation value is based on a solution to the system of three equations.

5. The method of claim 4, wherein:

the step of computing the heading rotation further comprises selecting the solution to the system of three equations that at least one of:

fulfills one or more predetermined biomechanical constraints, and results in an instantaneous heading error that:

is determined not to exceed a threshold value, and/or is less than an instantaneous heading error for another solution to the system of three equations; and the heading rotation value is based on the selected solution to the system of three equations.

6. The method of claim 1, further comprising providing a movement sequence of the person based on the orientation measurements provided by the first and second units wherein at least some orientation measurements of one of the first and second units have been modified.

7. The method of claim 1, further comprising repeating at least the computing and modifying steps one or more times with most recent orientation measurements provided by the first and second units for correction of heading error in the measurements provided by the units.

8. The method of claim 7, wherein the rotation applied in the step of modifying is at least further based on one or more heading rotation values previously computed for modification of previous orientation measurements.

9. The method of claim 1, further comprising, adjusting the arrangement of the first and second units on the first and second body members of the person, respectively.

10. The method of claim 1, wherein each of the first and second units comprises attaching devices for indicating or forcing arrangement of each unit with a predetermined orientation.

11. The method of claim 1, further comprising calibrating the first and second units after arranging them on the first and second body members.

12. The method of claim 1, wherein at least the second unit is arranged on the second body member such that one of three axes of the second unit is aligned or substantially aligned with a segment of the second body member.

13. The method of claim 1, wherein the first and second body members respectively are an upper arm and a forearm or vice versa, or the first and second body members respectively are a thigh and a shank or vice versa.

14. The method of claim 1, further comprising providing, by each of the first and second units, the orientation measurements to a user.

15. A motion tracking system comprising:

a computing device comprising at least one processor and at least one memory; and first and second inertial measurement units adapted to be arranged on first and second body members of a person and each at least comprising an accelerometer and a gyroscope;

the at least one processor being configured, together with the at least one memory, to:

obtain a first orientation measurement of the first unit;

compute a heading rotation value for containing the first orientation measurement within an axis plane of a joint connecting the first and second body members of the person based on a second orientation measurement of the second measurement unit; and modify the first orientation measurement or the second orientation measurement by applying a rotation based on the heading rotation value computed, to thereby correct for a heading rotation error of the first or second inertial measurement unit.

16. The motion tracking system of claim 15, wherein each of the first and second units further comprises a magnetometer.

17. The motion tracking system of claim 16, wherein each of the obtained orientation measurements comprise information obtained from the accelerometer, the gyroscope, and the magnetometer of each of the measurement units.

18. A computer program product that has instructions which, when executed by a computing device of a motion tracking system comprising a first and second inertial measurement units adapted to be arranged on first and second body members of a person and each at least comprising an accelerometer and a gyroscope, cause the computing device to:

obtain a first orientation measurement of the first unit;

compute a heading rotation value for containing the first orientation measurement within an axis plane of a joint connecting the first and second body members of the person based on a second orientation measurement of the second measurement unit; and modify the first orientation measurement or the second orientation measurement by applying a rotation based on the heading rotation value computed, to thereby correct for a heading rotation error of the first or second inertial measurement unit.

19. The computer program product of claim 18, wherein each of the first and second units further comprises a magnetometer.

20. The computer program product of claim 19, wherein each of the obtained orientation measurements comprise information obtained from the accelerometer, the gyroscope, and the magnetometer of each of the measurement units.

* * * * *